United States Patent
Egermann et al.

(10) Patent No.: US 7,333,892 B2
(45) Date of Patent: Feb. 19, 2008

(54) METHOD OF DETERMINING MULTIPHASE FLOW PARAMETERS OF A POROUS MEDIUM TAKING ACCOUNT OF THE LOCAL HETEROGENEITY

(75) Inventors: Patrick Egermann, Rueil Malmaison (FR); Roland Lenormand, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/212,760

(22) Filed: Aug. 29, 2005

(65) Prior Publication Data
US 2006/0047432 A1  Mar. 2, 2006

(30) Foreign Application Priority Data
Sep. 2, 2004  (FR) ................... 04 09273

(51) Int. Cl.
G01V 1/40 (2006.01)
G01N 15/08 (2006.01)
E21B 47/00 (2006.01)

(52) U.S. Cl. ............... 702/12; 73/38; 166/250.02

(58) Field of Classification Search ........... 702/12, 702/13; 703/2, 9; 73/38, 152.05–152.09, 73/153; 166/250.02, 275.02
See application file for complete search history.

(56) References Cited

U.S. PATENT DOCUMENTS

| | | | | |
|---|---|---|---|---|
| 4,506,542 A | * | 3/1985 | Rose .................. | 73/38 |
| 4,543,821 A | * | 10/1985 | Davis, Jr. .............. | 73/152.07 |
| 4,893,504 A | * | 1/1990 | O'Meara et al. ........ | 73/152.07 |
| 6,021,662 A | * | 2/2000 | Moulu et al. ........... | 73/38 |
| 6,823,297 B2 | * | 11/2004 | Jenny et al. ........... | 703/2 |

OTHER PUBLICATIONS

Egermann et al., Gas process Displacement Efficiency Comparisons on a Carbonate Reservoir, Jun. 9-12, 2003, Society of Petroleum Engineers 81577, pp. 1-13.*

P. Egermann et al., "Gas Process Displacement Efficiency Comparisons on a Carbonate Reservoir", 2003, Society of Petroleum Engineers Inc., pp. 1-13.

G.A. Virnovsky et al., "A Steady-State Upscaling Approach for Immiscible Two-Phase Flow", 2004, Kluwer Academic Publishers, pp. 167-192.

(Continued)

Primary Examiner—John Barlow
Assistant Examiner—Toan M. Le
(74) Attorney, Agent, or Firm—Antonelli, Terry, Stout & Kraus, LLP.

(57) ABSTRACT

A method with application for evaluation or production of a reservoir for determining multiphase flow parameters of a porous medium such as a rock, from the interpretation of displacement experiments. From an injection experiment on a rock sample, the saturation profiles are measured in different sections of the sample. The experimental data are then subjected to a preliminary interpretation by means of a numerical simulation code allowing production of simulated pressure profiles. These profiles are then combined with the measured saturation profiles so as to evaluate the local properties of the sample in terms of capillary pressure. These properties are then re-injected into the simulator as input data so as to finely interpret the flow parameters while respecting the evolutions of the differential pressure, of the displaced fluid production and of the saturation profiles.

36 Claims, 5 Drawing Sheets

OTHER PUBLICATIONS

J-M. Lombard et al., "Measurement Of Capillary Pressure Curves At Reservoir Conditions", Society of Core Analysts, Monterey, California, 2002, pp. 1-16.

H.M. Helset et al., "Relative Permeabilities from Displacement Experiments with Full Account for Capillary Pressure" SPE Reservoir Evaluation & Engineering, Apr. 1998, pp. 92-98.

* cited by examiner

METHOD OF DETERMINING MULTIPHASE FLOW PARAMETERS OF A POROUS MEDIUM TAKING ACCOUNT OF THE LOCAL HETEROGENEITY

BACKGROUND OF THE INVENTION

1. Field of the Invention

The present invention relates to a method of determining multiphase flow parameters of a porous medium such as a rock, from the interpretation of displacement experiments.

2. Description of the Prior Art

Determination of multiphase flow parameters, such as the relative permeabilities and the capillary pressure, is a major challenge within the context of oilfield development, whether in the reservoir evaluation or when starting production. Laboratory experiments carried out under reservoir pressure and temperature conditions are commonly performed to determine these parameters in a representative manner. In particular, the relative permeabilities are conventionally obtained by means of displacement experiments. The relative permeabilities are then obtained via an analytical and numerical experimental data interpretation so as to take account of all the physical phenomena (capillary pressure, gravity) that influence the experimental data obtained.

The following documents, mentioned in the course of the description hereafter, illustrate the state of the art:

- Courtial R. and Ghalimi S., "*Techniques for Relative Permeability Calculations: A Closer Look*", SCA No.2000-47, Society of Core Analysts, Abu-Dhabi, 2000,
- Dauba C., Hamon G., Quintard M. and Cherblanc F., "*Identification of Parallel Heterogeneities with Miscible Displacement*", SCA No.9933, Society of Core Analysts, Denver, Colo., 1999,
- Fincham A. and Gouth F., "*Improvements of Coreflood Design and Interpretation Using a New Software*", SCA No.2000-19, Society of Core Analysts, Abu-Dhabi, 2000,
- Goodfield M., Goodyear S. G. and Townsley P. H., "*New Coreflood Interpretation Method for Relative Permeabilities Based on Direct Processing of In-Situ Saturation Data*", SPE No.71490, Annual Technical Conference and Exhibition, New Orleans, La., 2001,
- Graue A., 1994, "*Imaging the Effects of Capillary Heterogeneities on Local Saturation Development in Long Corefloods*", SPE Drilling & Completion, v. March, pp. 57-64,
- Honarpour M. M., Cullick A. S. and Saad N., "*Influence of Small-Scale Rock Laminations on Core Plug Oil/Water Relative Permeability and Capillary Pressure*", SPE No.27968, Centennial Petroleum Engineering Symposium, Tulsa, OK, 1994,
- Mejia G. M., Mohanty K. K. and Watson A. T., 1995, "*Use of In-Situ Saturation Data in Estimation of Two-Phase Flow Functions in Porous Media*", Journal of Petroleum Science and Engineering, v. 12, pp. 233-245.

The commonest approach for determining the multiphase flow parameters of a porous medium such as a rock uses a homogeneous numerical model to describe the rock sample. The mean value of the petrophysical properties (permeability, porosity) of the sample is in this case assigned to any point thereof. A single relative permeabilities/capillary pressure set is also used for the entire sample. Displacement experiments are then interpreted by means of a flow simulator which essentially is an inversion loop. This inversion loop allows adjustment of the values of the multiphase flow parameters by minimizing an objective function expressing the difference between the simulation and the experimental results.

The local saturation data are then used globally with the other experimental data (differential pressure $\Delta P^i$ (t), displaced fluid production V(t)) to calculate the objective function. At each iteration, this function is minimized by adjusting the relative permeability curves (at the same time as the capillary pressure curves sometimes). Several publications have shown the added value of the local saturation measurements in the inversion process, in particular for low injected fluid saturation values (Courtial and Ghalimi, 2000). However, the numerical saturation profiles (from the flow simulator) can reproduce only globally the measured profiles since the numerical model is based on a homogeneous description. In other words, the local heterogeneity is not taken into account.

Now, it is well-known that this heterogeneity has an impact on local measurements. In fact, whatever the protocol chosen to select rock samples (CT-scanner, mercury-pump porosimetry, tracer test), the petrophyscial properties of these rocks are often heterogeneous at the scale of a core (Dauba et al., 1999). Various authors have furthermore shown the existence of atypical saturation profiles due to the presence of local heterogeneities within the sample used. Graue (1994) has detailed an interesting petrophysical survey carried out on an eolian sandstone initially considered to be homogeneous. It has been possible to interpret the origin of local saturation fluctuations from local permeability and capillary pressure values. Honarpour et al. (1994) have shown by means of several displacement experiments carried out on samples comprising laminations that the structure of the heterogeneity itself plays an important part in the shape of the relative permeability curves obtained by means of the usual interpretation process. These works show that the local heterogeneity of the rock actually affects the experimentally obtained saturation profiles.

Mejia and Mohanty (1995) have then suggested improving the previous procedure by inverting also the local capillary pressure value. Better fitting has thus been obtained but, as a result of the number of parameters to be adjusted within the scope of optimization, this approach is not very fast and in practice it is not applicable for saturation profiles comprising tens of points.

A more recent approach directly uses the saturation data (Goodfield et al., 2001). The specific feature of this approach is that it bypasses the local heterogeneity problem by smoothing the experimental saturation profiles and that it uses the profiles as input data for the numerical simulator. On the other hand, this approach leads to a noise-containing differential pressure in the course of time, which is not physical since it should always be smooth whatever the heterogeneity degree within the sample.

Another approach is detailed by Fincham and Gouth (2000), who present an interesting analysis of a multi-flow rate displacement experiment showing non-homogeneous saturation profiles. Reproduction of the local saturation fluctuations was improved by introducing several capillary pressure curves so as to take account of the local heterogeneity. Existing surveys have shown that this approach allows obtaining considerable interpretation quality gains but, since adjustment occurs manually, it is only applicable for a limited number of relative permeability/capillary pressure models.

Quite recent generalization of the acquisition of local saturation data has allowed considerable improvement of the degree of analysis and interpretation of the experiments carried out in petrophysics laboratories. SCAL (Special Core Analysis Laboratories) type experiments are then commonly mentioned. The saturation measurements are often affected by the local heterogeneities of the rock, thus exhibiting a non-smooth form which is difficult to reproduce by means of numerical simulation. The various methods currently available in the industry are not satisfactory because they do not take account of the existence of the local heterogeneity of the rock in the relative permeabilities inversion from the experimental data. The method hereafter overcomes this drawback with the double objective of improving the interpretation quality while taking account of the influence of the heterogeneity of the rock on the results obtained.

SUMMARY OF THE INVENTION

The invention relates to a method of determining multiphase flow parameters of a porous medium, such as the relative permeabilities and the capillary pressure, while taking account of the local heterogeneity of the medium, from experimental measurements resulting from at least one multi-flow rate type displacement experiment. This type of experiment injects a fluid into a sample of the medium initially saturated with chiefly one other fluid referred to as displaced fluid; during this experiment, the rate of injection of the injected fluid is increased at least once after a displaced fluid production stabilization.

The method comprises the following:
determining a local saturation profile of at least one of the fluids in at least one section of said sample;
determining, by means of a numerical flow simulator and for each section, a simulated capillary pressure profile fitted to the experimental measurements and the local saturation profile, from an initial set of relative permeability values as a function of the saturation and from a mean capillary pressure curve as a function of the saturation, deducing for each section a local capillary pressure curve as a function of the saturation, from local capillary pressure values obtained by combining the simulated capillary pressure profile and the local saturation profile;
determining an injected fluid relative permeability curve as a function of the saturation and a displaced fluid relative permeability curve as a function of the saturation for the entire sample, by means of the simulator and from the local capillary pressure curves.

According to the invention, to take account of the heterogeneity in the displaced fluid relative permeabilities, it is possible to complete the displaced fluid relative permeability curve by local displaced fluid relative permeability values by calculating the flow rates of the two fluids. Transient values of the local saturation profiles can thus be used.

According to the invention, the initial set of relative permeabilities can be determined by an analytical interpretation of the experimental measurements and of said local saturation profiles for each injection stage.

Within the scope of the invention, the mean capillary pressure curve can be determined on a sample close to the studied sample and having similar properties, for example from centrifugation experiments. This curve can then be normalized from capillary pressure values determined by analytical interpretation of the experimental measurements and of the local saturation profiles for each injection stage. Another way of normalizing this mean capillary pressure curve uses the Leverett function.

According to an embodiment, it is possible to determine the local capillary pressure curve only from the stabilized values of the local saturation profiles.

Finally, according to the invention, the local capillary pressure curve can be determined by normalizing the mean capillary pressure curve as a function of the saturation by the local capillary pressure values.

BRIEF DESCRIPTION OF THE DRAWINGS

Other features and advantages of the method according to the invention will be clear from reading the description hereafter, given by way of non limitative example, with reference to the accompanying figures wherein.

DETAILED DESCRIPTION OF THE INVENTION

The method according to the invention allows interpretation of multiphase flow parameters of a porous medium such as a rock, from displacement experiments. The method furthermore allows evaluation of the impact of the local heterogeneity of the porous medium on multiphase flow parameters such as the capillary pressure and the relative permeabilities.

The method uses pressure data rather than saturation data to characterize the local heterogeneity of the samples.

In fact, the pressure is less sensitive than the saturation to local heterogeneities. Interpretation of a displacement experiment only from the mean properties of the sample, while taking account of the heterogeneities, is possible because the pressure profiles can be evaluated in a satisfactory manner. It is then possible to use these simulated local pressure values in combination with the measured local saturation values to explicitly obtain local capillary pressure values.

Described here in detail is the structure and the method of operation of the various interpretation stages involved in the invention, which can be split up into four major stages:

1. Acquisition of experimental data resulting from a multi-flow rate displacement experiment.
2. Determination, by analytical interpretation of the experimental data and for each injection stage, of the inlet saturation $S^i$ and for each of these saturations determination of the inlet capillary pressure $P_c^i(S^i)$ and of the injected fluid relative permeability $kr_{inj}(S^i)$, of the outlet saturation $S^o$ and of the displaced fluid relative permeability $kr_{dep}(S^o)$.
3. Estimation of capillary pressure profiles by fitting of the differential pressure and of the production by means of a flow simulator, without taking account of the heterogeneities.
4. Adjustment of the set of relative permeabilities by means of a flow simulator, while taking account of the heterogeneities.

Acquisition of Experimental Data Resulting from a Multi-flow Rate Displacement Experiment A multi-flow rate displacement experiment injects a fluid (referred to as injected fluid) into a rock sample initially saturated with chiefly one other fluid (referred to as displaced fluid). The rate of injection is increased several times after stabilization, and for each stabilization the evolution of the following parameters, which constitute the experimental data, is measured:
- the differential pressure, for one of the fluids, on either side of the sample, denoted by $\Delta P^i(t)$ (intermediate pressure measurements are not necessary),
- the production of the displaced fluid, denoted by $V(t)$,
- the local saturation profiles for one of the two fluids (injected or displaced), at certain points or sections ($x_1$, $x_2$, $x_3$, . . . ), denoted by $S(x_1,t), S(x_2,t), \ldots$ The injected fluid can be, for example, water and the displaced fluid can be oil.

Analytical Interpretation of the Experimental data

An analytical interpretation of the experimental data thus measured is then carried out. The stabilization state corresponding to an equilibrium between the viscous forces and the capillary forces becomes possible to evaluate, for a given saturation value, the mean value of the capillary pressure at the scale of the analyzed sample, denoted by Pc, the mean value of the injected fluid relative permeability, denoted by $kr_{inj}$, and the mean value of the displaced fluid relative permeability, denoted by $kr_{dep}$. It is therefore possible to use, for example, the expressions developed within the context of the semi-dynamic method described in French patent 2,708, 742 filed by the assignee.

In this method, the inlet saturation of the sample ($S_i$) is determined by means of the formula as follows:

$$S^i(\Delta P^i) = \overline{S} + q \frac{d\overline{S}}{dq} \quad (1)$$

where:
$S^i$ is the inlet saturation
q is the flow rate of the fluid injected into the sample
$\Delta P^i$ is the differential pressure measured at the sample inlet
$\overrightarrow{S}$ is the mean saturation of one of the two fluids. $\overrightarrow{S}$ can be obtained by averaging the local saturation values measured experimentally ($S(x_1,t), S(x_2,t), \ldots$) or calculated from the production of the displaced fluid measured at the outlet of the sample ($V(t)$).

At the end of each injection period, when stabilization is reached, it is important to note that the pressure at the level of the displaced fluid is uniform and equal to the outlet pressure ($P_{dep}^o$). Thus, the local pressure of the injected fluid directly corresponds to the capillary pressure plus the outlet pressure. In cases where stabilization is not completely reached (pressure in the displaced fluid non-uniform), it has to be noted that the pressure profiles in the two fluids are smooth and that it is also possible to directly use the simulated capillary pressure profiles to deduce the local properties.

Thus, at the sample outlet, the pressure of the injected fluid is considered to be equal to the pressure of the displaced fluid. Insofar as the capillary pressure is defined as the difference between these two pressures, the capillary pressure at the outlet ($P_c^o$) is zero: $P_c^o=0$.

At the sample inlet, if the displaced fluid pressure is zero ($P_{dep}^o=0$), the differential pressure at the inlet, which corresponds to the inlet pressure of the injected fluid, is equal to the capillary pressure at the inlet ($P_c^i$): $P_c^i=\Delta P^i (P_c^i=\Delta P^i + P_{dep}^o$ if $P_{dep}^o \neq 0$)

Thus, at each stage, an inlet saturation $S^i$ is calculated and the differential pressure at the inlet, which corresponds to the capillary pressure at the inlet, is measured. Thus obtained are a set of pairs, one for each stage, ($S^i$; $P_c^i$).

The quantity $kr_{inj}$ is determined by means of the formula as follows, for a given inlet saturation and therefore a given $\Delta P^i$ (for each stage):

$$kr_{inj} = \frac{\mu L}{KA} \frac{dq}{d\Delta P^i} \quad (2)$$

where:
$\mu$ is the viscosity of the injected fluid
L is the length of the sample
K is the permeability
A is the injection surface.

To determine $kr_{dep}$, it is possible to use a JBN type interpretation known in the art, and described for example in the following document:
Johnson E. F., Bossler D. P. and Naumann V. O.: "*Calculation of Relative Permeability from Displacement Experiments*", Trans. AIME, 216, 370-372, 1959.

This method requires measurement of the outlet saturation $S^o$.

Thus obtained, for each injection stage, is a saturation $S^i$, $P_c^i(S^i)$, $kr_{inj}(S^i)$ and $kr_{dep}(S^o)$. The whole of the displaced fluid and injected fluid relative permeabilities is denoted by krs(S).

Simulation of Capillary Pressure Profiles Without the Heterogeneities Being Taken into Account After evaluating at each stage a saturation value ($S^i$), a mean capillary pressure value ($P_c^i(S^i)$), an injected fluid relative permeability value ($kr_{inj}(S^i)$) and a displaced fluid relative permeability value ($kr_{dep}(S^o)$), and a stage of numerical interpretation of the experimental measurements is carried out without the heterogeneities being taken into account. The goal is to determine, by simulation, pressure profiles (for each section $x_1$, $x_2$, . . . ) in the two fluids representative of the experimental measurements, referred to as simulated profiles. The simulated capillary pressure $P_c^{sim}(x,t)$ ($x=x_1, x_2, \ldots$) is obtained by the difference between the two profiles. This simulation is performed by means of a flow simulator. A flow simulator allows, from data referred to as input data, interpretation of the experimental data in terms of relative permeabilities. A simulator comprises in particular an inversion loop allowing best adjustment of this set of relative permeabilities so that the data calculated from these relative permeabilities, such as the differential pressure ($\Delta P^i(t)$), the production (V(t)), the saturation (S(t)) and the pressures of each fluid, by means of equations governing the flows, best fits the experimental data (the minimum of an objective function is then reached). Conventionally, the simulator is supplied with the relative permeabilities (obtained for example by means of an analytical interpretation) and the capillary pressures, then the differential pressure ($\Delta P^i(t)$) and the production (V(t)), among other things, are simulated. The simulated values are then compared with the measured values and the relative permeability values are adjusted accordingly. In the method according to the invention, this simulation stage is used essentially to determine a capillary pressure profile ($P_c^{sim}(x, t)$ ($x=x_1, x_2, \ldots$)). The relative permeability values resulting therefrom will be adjusted in the next stage to take account of the heterogeneities.

The procedure is then as follows:

Determining, for example by means of centrifugation experiments known in the art, a curve of mean capillary pressure values as a function of the saturation, on a sample close to the sample studied and having similar properties is obtained. This curve is denoted by $P_c^V(S)$.

Curve $P_c^V(S)$ is fined down. A first method takes account of the permeability, porosity and interfacial tension variations via the Leverett function. This function is described in the following documents:

Leverett M. C.: "*Capillary Behavior in Porous Solids*", Trans. AIME, 142, 152-168, 1941;

Leverett M. C., Lewis W. B. and True M. E.: "*Dimensional Model Studies of Oilfield behavior*", Trans. AIME, 146, 175-193, 1942.

A second method uses the results of the analytical interpretation stage of the multi-flow rate displacement experiment. In fact, any allowing calculation of capillary pressure values ($P_c^i(S^i)$) for a certain saturation number (inlet capillary pressure and inlet saturation for each injection stage), it is possible to normalize the capillary pressure curve $P_c^V(S)$ from these points that is curve $P_c^V(S)$ is deformed so as to pass through these points precisely calculated on the sample studied. This normalized curve is denoted by $P_C(S)$.

Then, by means of $P_C(S)$ and of the initial set of krs(S) from the analytical interpretation of the experimental data, the simulator is used to fit the experimental data ($\Delta P^i(t)$) and (V(t)) by deforming the krs(S) curves until the minimum of an objective function is obtained. The simulated capillary pressure profiles ($P_c^{sim}(x,t)$ ($x=x_1, x_2, \ldots$)) are determined at the same time directly from the numerical outputs of the simulation.

At the end of this first numerical interpretation obtained is a set of krs(S) corresponding to a first fitting of the differential pressure ($\Delta P^i(t)$), of the production curves (V(t)), and of representative simulated pressure profiles or, in an equivalent manner, of simulated capillary pressures ($P_c^{sim}(x,t)$ ($x=x_1, x_2, \ldots$)). The heterogeneities have not yet been taken into account.

Adjustment of the Relative Permeabilities with the Heterogeneities Being Taken into Account The original feature of the method uses the pressure data rather than the saturation data for characterizing the local heterogeneity of the samples. This approach is mathematically justified by the fact that the pressure equation is parabolic (or elliptical) whereas the saturation equation is of hyperbolic type, as shown in the following document:

Guérillot D. and Verdière S., "*Different Pressure Grids for Reservoir Simulation in Heterogeneous Reservoirs*", SPE No. 29148, 13$^{th}$ SPE Symposium on Reservoir Simulation, San Antonio, Tex., 1995.

The pressure data are thus naturally smoother than the saturation data in the presence of heterogeneities. The pressure is less sensitive than the saturation to local heterogeneities.

Within the context of the interpretation of experiments carried out on samples comprising local heterogeneities, the pressure profiles can thus be reasonably estimated from a numerical simulation in each section where the local saturation is measured, even if no local pressure measuring device is available.

It is thus possible to evaluate in a satisfactory manner, while taking into account of the heterogeneity, the pressure profiles and therefore the capillary pressure profiles by means of only the mean properties of the sample corresponding to a homogeneous rough description.

First determined are the local capillary pressure values ($P_C(x_1,t)$, $P_C(x_2,t)$, $\ldots$) by combining the simulated capillary pressure profiles ($P_c^{sim}(x,t)$ ($x=x_1,x_2,\ldots$)) and the saturation profiles measured at the end of each injection period in stabilized regime ($S(x_1,t)$, $S(X_2,t)$, $\ldots$). Then deduced therefrom are several local capillary pressure values for each section where a saturation was measured: $P_C(x,S), x=x_1,x_2,\ldots$ Then, these calculated local capillary pressure values ($P_C(x,S)$, $x=x_1, x_2, \ldots$) are used to renormalize locally the mean original capillary pressure curve used within the context of the first simulation under homogeneous conditions ($P_C(S)$).

These various capillary pressure curves determined for each section ($P_C(x_1,S)$, $P_C(x_2,S)$, $\ldots$) are thereafter re-injected into the simulator as input data so as to describe the heterogeneity.

Finally, this new data set of krs(S), $P_C(x_1,S)$, $P_C(x_2, S)$ $\ldots$ is optimized again by acting upon the curves of krs(S) only, which makes the inversion loop very fast.

The procedure for calculating the local capillary pressures for each section ($P_C(x_1,S)$, $P_C(x_2,S)$, $\ldots$) c an be repeated several times, but practice has shown that one iteration is often sufficient to obtain a very satisfactory result.

At this point, the local capillary pressure curves have been introduced in the simulator to take account of the heterogeneity regarding the saturations, and an injected fluid permeability curve taking account of the heterogeneities and a displaced fluid permeability curve taking account of the heterogeneities for the entire sample have been determined by inversion.

It is then necessary to take account of the heterogeneity regarding the displaced fluid relative permeabilities, that is to determine local values for $kr_{dep}$.

Determination of the Local Displaced Fluid Relative Permeability Values

Local displaced fluid relative permeability values are determined on the basis of the transient measured saturation profiles (only the profiles stabilized at the end of the injection periods, and no intermediate profiles, have been used so far).

The transient measured saturation profiles corresponding to the local saturation variation with time ($S(x_1,t)$, $S(x_2,t)$, $\ldots$) allow calculation of the flow rates of the injected and displaced fluids, and therefore the local value of the fractionary flow ($f_{inj}$) is equal by definition to the flow rate ($Q_{inj}$) of a fluid divided by the total flow rate ($Q_t$):

$$f_{inj} = \frac{1 - \frac{K}{u_t} \frac{kr_{dep}}{\mu_{dep}} \frac{\partial P_c}{\partial L}}{1 + \frac{\mu_{inj}}{\mu_{dep}} \frac{kr_{dep}}{kr_{inj}}} \qquad (4)$$

It is then possible to determine the local values of the displaced fluid relative permeabilities ($kr_{dep}$) from Equation (4) as follows:

$$f_{inj} = \frac{Q_{inj}}{Q_t} \qquad (3)$$

where:
$\mu_{inj}$ is the viscosity of the injected fluid
$\mu_{dep}$ is the viscosity of the displaced fluid
L is the length of the sample
K is the permeability of the sample
$u_t$ is the total filtration rate (that is the total flow rate of the two fluids divided by the surface of flow)
$P_c$ is the capillary pressure profile in the course of time ($P_c(x,t)$)

It should be noted that gravity forces are disregarded in this expression. The capillary pressure profile in the course of time ($P_c(x,t)$) is given by the flow simulation and the curve $kr_{inj}$ considered is the curve obtained by the previous procedure for determining the local injected fluid relative permeability values.

Thus, the method according to the invention allows improving the interpretation of displacement experiments in terms of relative permeabilities carried out on porous media by taking account, in a simple and fast manner, of all of the information collected by measuring the local saturations along the sample. The present method is particularly suited for interpretation of multi-flow rate type experiments during which the injection rate is increased several times after stabilization. It comprises several interpretation levels involving analytical formulas and numerical simulation tools. The simulated pressure profiles are combined with the measured stabilized saturation profiles so as to evaluate the local properties of the sample in terms of capillary pressure. These properties are then re-injected into the simulator as input data so as to finely interpret the flow parameters (krs(S)) while respecting at the same time the evolutions of the differential pressure, of the displaced fluid production and of the saturation profiles.

The present invention allows evaluation and quantification of the impact of the local heterogeneity of the rock on the flow parameters, such as the capillary pressure and the relative permeabilities, from the local saturation fluctuations that are commonly observed during laboratory experiments. Both stabilized and transient saturation profiles are used. These results can be obtained from data resulting from a single experiment whereas a large number of experiments on samples with similar properties would be necessary to obtain the same information with a conventional approach.

It is also possible to evaluate the confidence interval on the flow parameters, which is particularly useful for feeding input data to uncertainty computing softwares at the reservoir scale.

The saturation fluctuations are taken into account in a fine manner without extending the relative permeability inversion procedure. Furthermore, the method is based on the use of simulated pressure profiles, which is physically justified since the pressure variations are naturally less sensitive to heterogeneities than the saturation.

The method is simple and fast because the inversion involves only the curves of krs(S), the local capillary pressure values being determined analytically from the simulated pressure data and the measured saturations.

The method is applicable for revisiting existing experimental data comprising local saturation measurements and several injection rates, or for processing any new experiment even if the saturation profiles consist of a large number of experimental points.

Application to Real Cases
Gas/Oil Case

The experimental data presented in this part are relative to a nitrogen injection under ambient conditions into a core consisting of 4 samples arranged end to end (composite). The mean porosity of the sample is 30%, whereas the permeability is 10 mD. Initially, the sample is oil saturated with irreducible water (of the order of 10%). The injection experiment was carried out using a scanner, which allows measurement of the evolution of the saturation profiles during the experiment. The nitrogen was injected at imposed pressure in three stages: 1 bar, 3 bars and 8 bars differential pressure. At the outlet, the effluents produced were measured during the experiment.

Figure 1A:
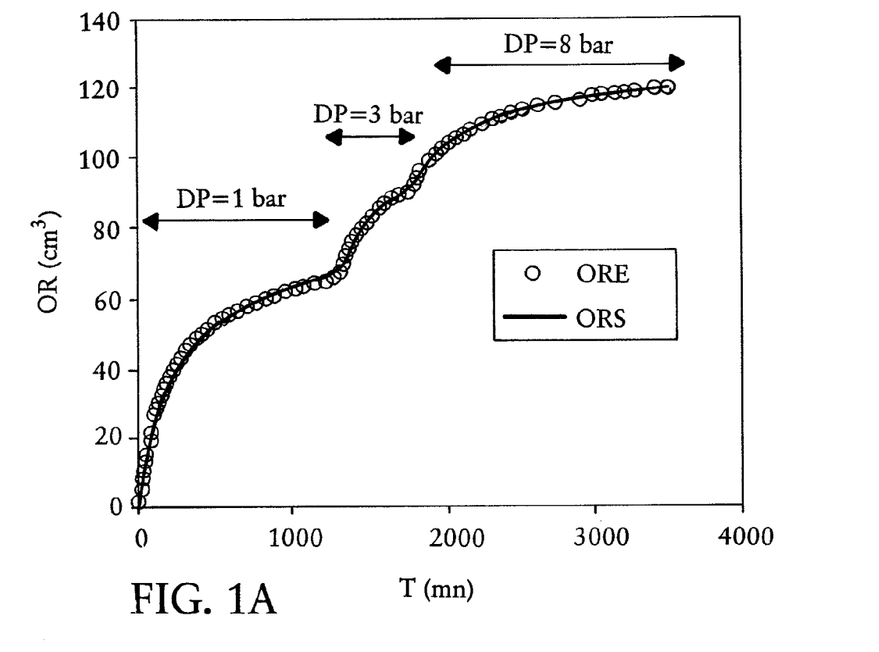
FIGS. 1A and 1B show fitting of the gas and oil production obtained from a conventional approach.
Figure 1B:
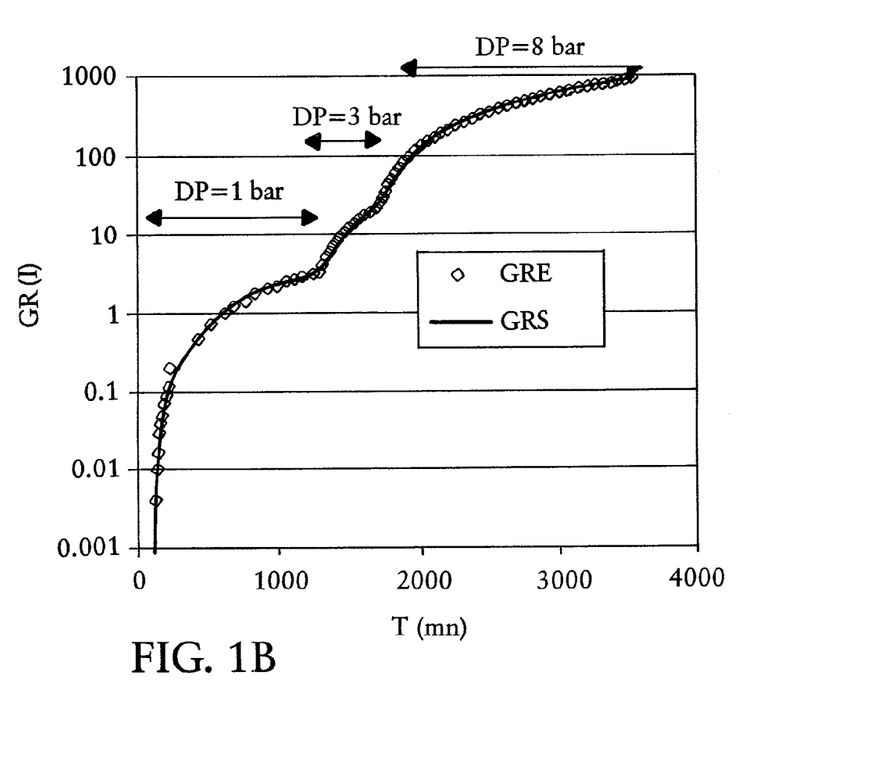
Figure 2A:
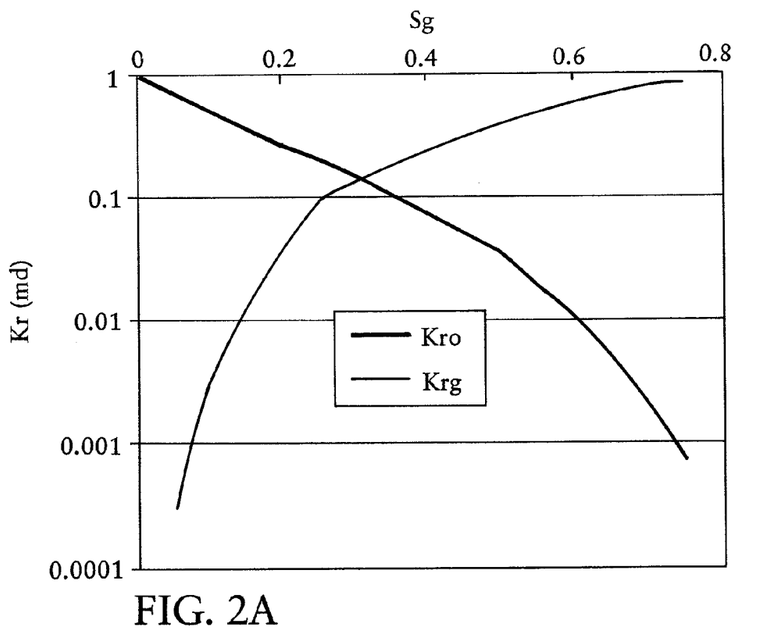
FIG. 2A shows the gas/oil relative permeability curves obtained within the context of this interpretation, the general shape of the curves being conventional.
Figure 2B:
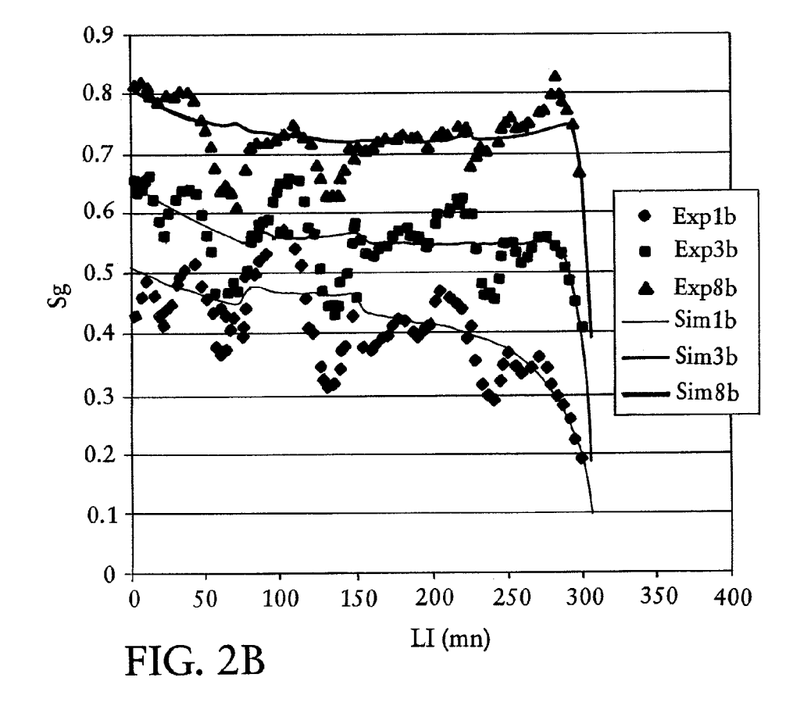
FIG. 2B shows the simulated saturation profiles obtained with the conventional approach, a good general agreement being observed, but the fluctuations are not reproduced.

The homogeneous interpretation of the method as described in the previous part has allowed obtaining, with a coherent set of relative gas (Krg) and oil (Kro) permeabilities (FIG. 2A), satisfactory fitting of the production curves, as shown by FIGS. 1A and 1B. In fact, the curves of FIG. 2A, show the relative permeability (Kr) as a function of the gas saturation (Sg), have a conventional shape. Furthermore, FIG. 1A, whose abscissa axis represents the time (T) and whose ordinate axis represents the oil production (OR), shows very good fitting between the simulated oil production curve (ORS) and the experimental oil production curve (ORE), for the various injections characterized by their differential pressure DP at 1 bar, 3 bars and 8 bars. Similarly, FIG. 1B, whose abscissa axis represents the time (T) and whose ordinate axis represents the gas production (GR), shows very good fitting between the simulated gas production curve (GRS) and the experimental gas production curve (GRE), for the various injection stages characterized by their differential pressure at 1 bar, 3 bars and 8 bars. On the other hand, it can be seen that the simulated saturation profiles agree with the measured saturations only globally, the local fluctuations being not well reproduced, as illustrated in FIG. 2B. FIG. 2B shows the gas saturation (Sg) at different points characterized by their distances from the sample inlet (LI). The experimental values (Exp) for different injection stages characterized by the outlet pressure (1 bar (Exp1b), 3 bars (Exp3b) and 8 bars (Exp8b) can be observed. It is also possible to observe the corresponding simulated curves: Sim1b, Sim3b and Sim8b.

Figure 3A:
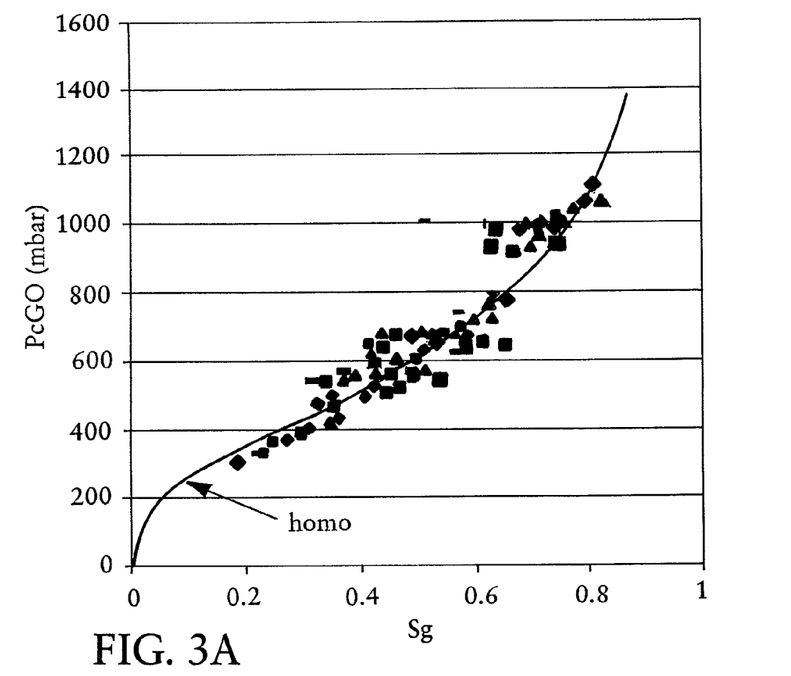
FIG. 3A shows the local capillary pressure values obtained using the proposed approach, the cluster resulting from the compilation of 100 saturation measurement points, and the values obtained furthermore agreeing with the global capillary pressure curve obtained from this sample.
Figure 3B:
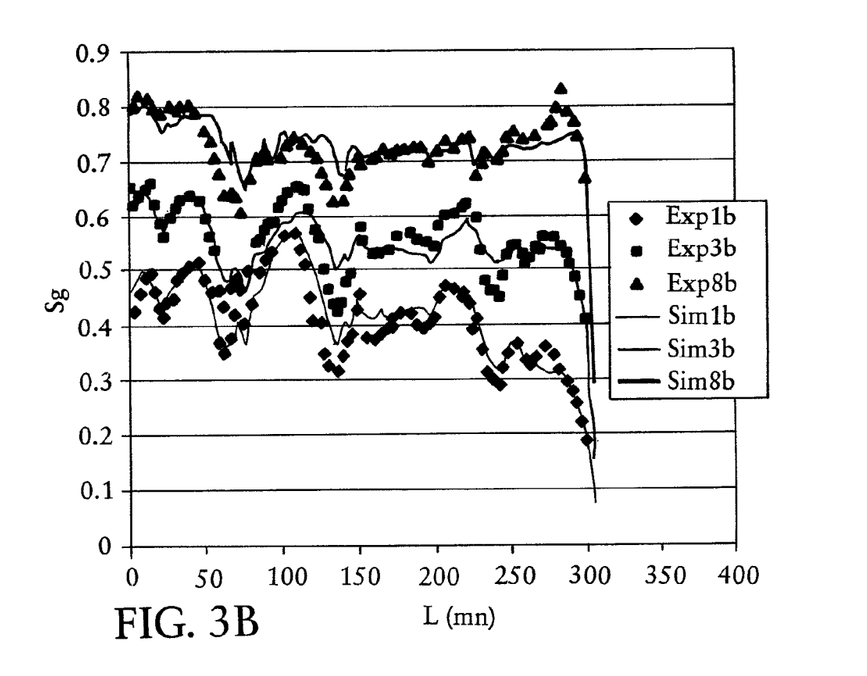
FIGS. 3B shows the simulated saturation profiles obtained with the proposed approach, a very good agreement being observed with the local measurements and the fluctuations being very well reproduced.
Figure 4A:
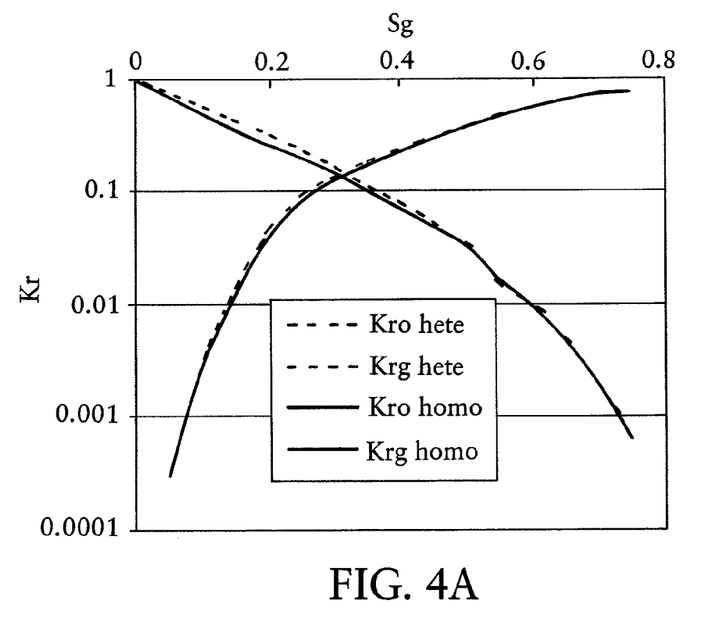
FIG. 4A shows the gas/oil relative permeability curves obtained within the scope of the new approach.
Figure 4B:
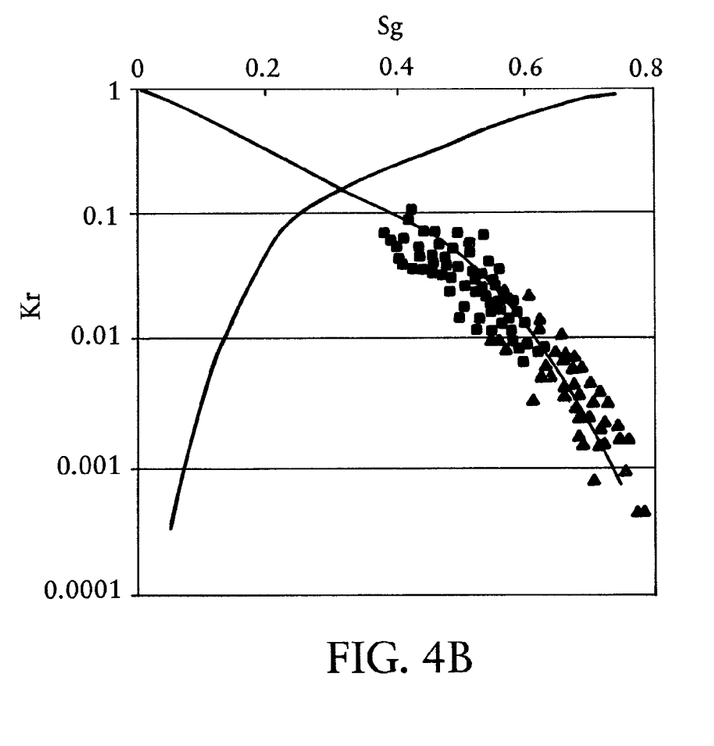
FIG. 4B shows the use of the transient saturation profiles for calculating the local values of the displaced fluid relative permeability (kro in this case), the results obtained showing good agreement with the global curve obtained by simulation.

The heterogeneous stage allows calculation of a large number of local capillary pressure points as shown in FIG. 3A, which represents the gas/oil capillary pressure (PcGO) as a function of the gas saturation (Sg). The points obtained are in good agreement with the global curve (homo) used within the context of the homogeneous approach, but the fluctuations reflect the heterogeneity level within the sample. The use of these local capillary pressure data in the simulator then leads to a dramatic improvement in the saturation profile calibration quality, as shown by FIG. 3B which can be compared with FIG. 2B. As illustrated by FIG. 4A, the new set of relative permeabilities obtained after the optimization stage ("Kro hete" and "Krg hete") is not very different from the homogeneous case ("Kro homo" and "Krg homo"). Besides, calculation of the local fractionary flow allows evaluation of local values for the displaced fluid relative permeability (FIG. 4B). Implementation of the invention thus allows both improvement of the fitting quality of the experiment and evaluating of the impact of the local heterogeneities on the multiphase flow parameters such as capillary pressure and relative permeabilities.

Water/Oil Case

This second application example relates to a brine injection (imbibition) into a short sample initially at $S_{wi}$. The experiment was carried out on a carbonate rock (of porosity 29% and of permeability 14.8 mD) using 4 injection periods.

Figure 5A:
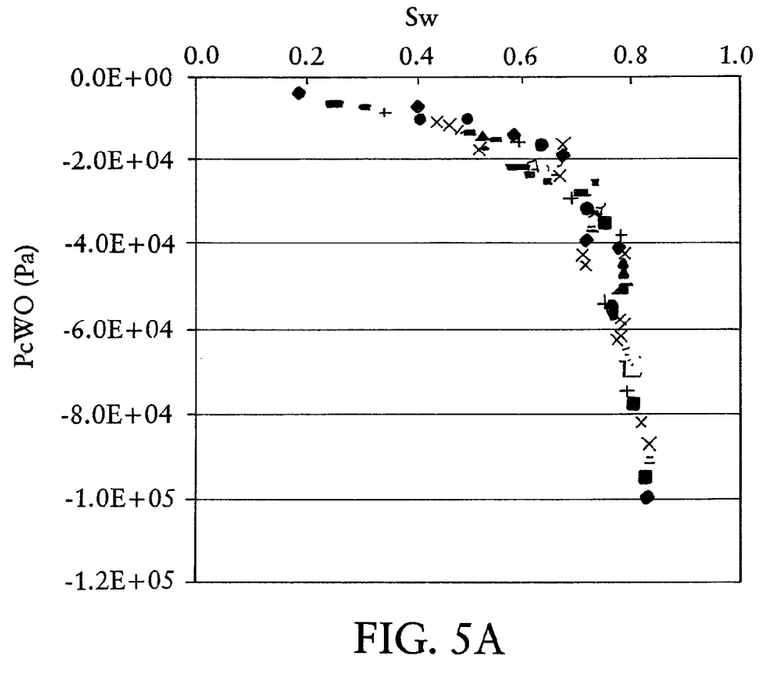
FIG. 5A shows the local capillary pressure curves obtained using the invention in a water/oil case.
Figure 5B:
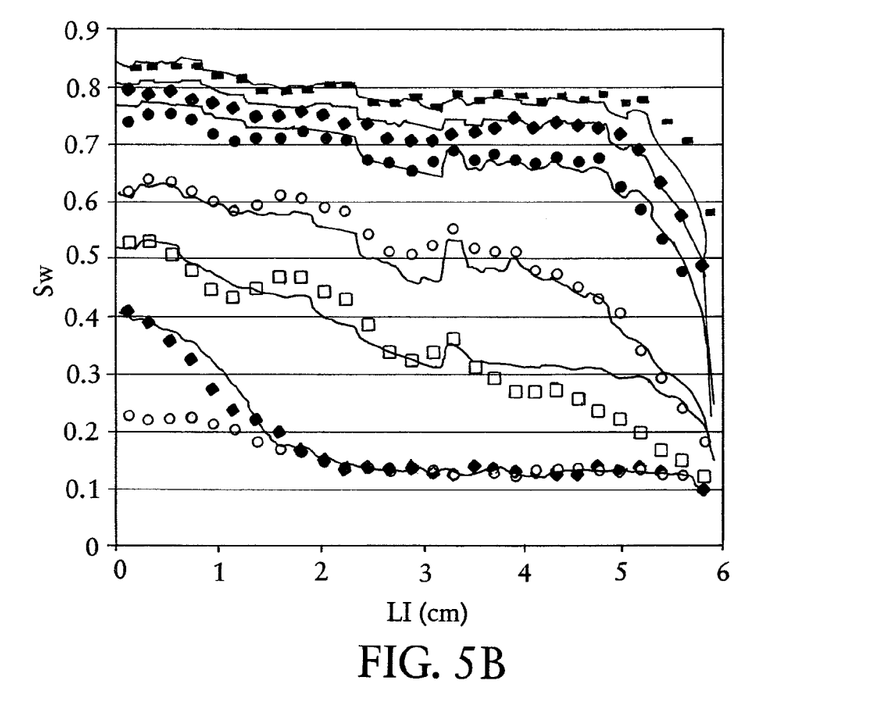
FIG. 5B shows the simulated saturation profiles obtained with the invention in the water/oil case, a very good agreement being observed with the measured local saturations.

FIG. 5A (where PcWO is the brine/oil capillary pressure) shows the local capillary pressure points obtained by applying the proposed method. These points correspond to negative capillary pressure values over the entire saturation range, which suggests that the sample is rather oil wet. Introduction of these data into the simulator has allowed obtaining simulated saturation profiles in very good agreement with the measured data (FIG. 5B, where Sw is the brine saturation), which again in this case shows the added value of the proposed method.

The invention claimed is:

1. A method for developing or evaluating an oil field by carrying out laboratory experiments to determine multiphase flow parameters of the oil field while taking account of local heterogeneity of the oil field, from experimental measurements resulting from at least one multi-flow rate type displacement experiment of injecting a fluid into a sample of the oil field initially saturated with one other displaced fluid during which a rate of injection of the injected fluid is increased at least once after a displaced fluid production stabilization, comprising:
    determining a local saturation profile of at least one of the fluids in at least one section of the sample;
    determining, by means of a numerical flow simulator, and for each section, a simulated capillary pressure profile fitted to the experimental measurements and the local saturation profile, from an initial set of relative permeability values as a function of the saturation and from a mean capillary pressure curve as a function of the saturation;
    deducing, for each section, a local capillary pressure curve as a function of the saturation, from local capillary pressure values obtained by combining the simulated capillary pressure profile and the local saturation profile;
    determining an injected fluid relative permeability curve, as a function of the saturation and a displaced fluid relative permeability curve as a function of the saturation for the entire sample, by means of the simulator and from the local capillary pressure curves; and
    using the injected relative fluid permeability curve to evaluate the oil field or to provide production of oil from the oil field.

2. A method claimed in claim 1, wherein the multiphase flow parameters of the porous medium comprise relative permeability and capillary pressure.

3. A method as claimed in claim 1, wherein a displaced fluid relative permeability curve is completed by local displaced fluid relative permeability values by calculating flow rates of the fluids by means of transient values of the local saturation profile.

4. A method as claimed in claim 1, wherein an initial set of relative permeabilities is determined by an analytical interpretation of the experimental measurements and of the local saturation profile for each injection stage.

5. A method as claimed in claim 1, wherein the mean capillary pressure curve is determined on a sample close to the sample and having related properties.

6. A method as claimed in claim 1, wherein the mean capillary pressure curve is determined by means of and centrifugation experiment.

7. A method as claimed in claim 1, wherein the mean capillary pressure curve is normalized from capillary pressure values determined by analytical interpretation of the experimental measurements and of the local saturation profile for each injection stage.

8. A method as claimed in claim 1, wherein the mean capillary pressure curve is normalized from a Leverett function.

9. A method as claimed in claim 1, wherein the local capillary pressure curve is determined from stabilized values of the local saturation profile.

10. A method as claimed in previous claim 1, wherein the local capillary pressure curve is determined by normalizing the mean capillary pressure curve as a function of the saturation by the local capillary pressure values.

11. A method as claimed in claim 2, wherein the mean capillary pressure curve is normalized from capillary pressure values determined by analytical interpretation of the experimental measurements and of the local saturation profile for each injection stage.

12. A method as claimed in claim 2, wherein the mean capillary pressure curve is normalized from a Leverett function.

13. A method as claimed in claim 2, wherein the local capillary pressure curve is determined from stabilized values of the local saturation profile.

14. A method as claimed in previous claim 2, wherein a local capillary pressure curve is determined by normalizing the mean capillary pressure curve as a function of the saturation by the local capillary pressure values.

15. A method as claimed in claim 3, wherein the mean capillary pressure curve is normalized from capillary pressure values determined by analytical interpretation of the experimental measurements and of the local saturation profile for each injection stage.

16. A method as claimed in claim 3, wherein the mean capillary pressure curve is normalized from a Leverett function.

17. A method as claimed in claim 3, wherein the local capillary pressure curve is determined from stabilized values of the local saturation profile.

18. A method as claimed in previous claim 3, wherein the local capillary pressure curve is determined by normalizing the mean capillary pressure curve as a function of the saturation by the local capillary pressure values.

19. A method as claimed in claim 4, wherein the mean capillary pressure curve is normalized from capillary pressure values determined by analytical interpretation of the experimental measurements and of the local saturation profile for each injection stage.

20. A method as claimed in claim 4, wherein the mean capillary pressure curve is normalized from a Leverett function.

21. A method as claimed in claim 4, wherein the local capillary pressure curve is determined from stabilized values of the local saturation profile.

22. A method as claimed in previous claim 4, wherein the local capillary pressure curve is determined by normalizing the mean capillary pressure curve as a function of the saturation by the local capillary pressure values.

23. A method as claimed in claim 5, wherein the mean capillary pressure curve is normalized from capillary pressure values determined by analytical interpretation of the experimental measurements and of the local saturation profile for each injection stage.

24. A method as claimed in claim 5, wherein the mean capillary pressure curve is normalized from a Leverett function.

25. A method as claimed in claim 5, wherein the local capillary pressure curve is determined from stabilized values of the local saturation profile.

26. A method as claimed in previous claim 5, wherein the local capillary pressure curve is determined by normalizing the mean capillary pressure curve as a function of the saturation by the local capillary pressure values.

27. A method as claimed in claim 6, wherein the mean capillary pressure curve is normalized from capillary pressure values determined by analytical interpretation of the experimental measurements and of the local saturation profile for each injection stage.

28. A method as claimed in claim 6, wherein the mean capillary pressure curve is normalized from a Leverett function.

29. A method as claimed in claim 6, wherein the local capillary pressure curve is determined from stabilized values of the local saturation profile.

30. A method as claimed in previous claim 6, wherein the local capillary pressure curve is determined by normalizing the mean capillary pressure curve as a function of the saturation by the local capillary pressure values.

31. A method as claimed in claim 7, wherein the mean capillary pressure curve is normalized from a Leverett function.

32. A method as claimed in claim 7, wherein the local capillary pressure curve is determined from stabilized values of the local saturation profile.

33. A method as claimed in previous claim 7, wherein the local capillary pressure curve is determined by normalizing the mean capillary pressure curve as a function of the saturation by the local capillary pressure values.

34. A method as claimed in claim 8, wherein the local capillary pressure curve is determined from stabilized values of the local saturation profile.

35. A method as claimed in previous claim 8, wherein the local capillary pressure curve is determined by normalizing the mean capillary pressure curve as a function of the saturation by the local capillary pressure values.

36. A method as claimed in previous claim 9, wherein the local capillary pressure curve is determined by normalizing the mean capillary pressure curve as a function of the saturation by the local capillary pressure values.

* * * * *